(12) United States Patent
Schabbach et al.

(10) Patent No.: US 10,569,012 B2
(45) Date of Patent: Feb. 25, 2020

(54) DRUG DELIVERY DEVICE WITH DISPOSABLE CARTRIDGE AND DISPOSABLE INJECTOR

(71) Applicant: Sanofi-Aventis Deutschland GMBH, Frankfurt am Main (DE)

(72) Inventors: Michael Schabbach, Frankfurt am Main (DE); Olaf Zeckai, Weinheim (DE); Meinolf Werner, Worms (DE)

(73) Assignee: Sanofi-Aventis Deutschland GMBH, Frankfurt am Main (DE)

(*) Notice: Subject to any disclaimer, the term of this patent is extended or adjusted under 35 U.S.C. 154(b) by 143 days.

(21) Appl. No.: 15/104,913

(22) PCT Filed: Dec. 18, 2014

(86) PCT No.: PCT/EP2014/078412
§ 371 (c)(1),
(2) Date: Jun. 15, 2016

(87) PCT Pub. No.: WO2015/091760
PCT Pub. Date: Jun. 25, 2015

(65) Prior Publication Data
US 2016/0317737 A1 Nov. 3, 2016

(30) Foreign Application Priority Data
Dec. 20, 2013 (EP) .................................... 13198765

(51) Int. Cl.
*A61M 5/148* (2006.01)
*A61M 5/162* (2006.01)
*A61M 5/142* (2006.01)

(52) U.S. Cl.
CPC ........ *A61M 5/148* (2013.01); *A61M 5/14232* (2013.01); *A61M 5/14244* (2013.01); *A61M 5/162* (2013.01); *A61M 2005/14268* (2013.01)

(58) Field of Classification Search
CPC ......... A61M 2005/14252; A61M 2005/14256; A61M 2005/14268; A61M 5/14232;
(Continued)

(56) References Cited

U.S. PATENT DOCUMENTS

| | | | |
|---|---|---|---|
| 6,752,785 B2* | 6/2004 | Van Antwerp | A61M 5/16836 604/111 |
| 2008/0255516 A1* | 10/2008 | Yodfat | A61M 5/14248 604/151 |

(Continued)

FOREIGN PATENT DOCUMENTS

| | | |
|---|---|---|
| DE | 102006047613 | 4/2008 |
| EP | 0019817 | 12/1980 |

(Continued)

OTHER PUBLICATIONS

International Preliminary Report on Patentability in International Application No. PCT/EP2014/078412, dated Jun. 21, 2016, 5 pages.
(Continued)

*Primary Examiner* — Quynh-Nhu H. Vu
(74) *Attorney, Agent, or Firm* — Fish & Richardson P.C.

(57) ABSTRACT

The present invention relates to a drug delivery device for dispensing a liquid medicament, comprising: a housing (12) having at least one feeder member (100), a disposable injector (60) comprising an injection needle (65), a flexible tube (64) and an injector fluid coupling (68), wherein the injection needle (65) is in fluid communication with the fluid coupling (68) via the flexible tube (64), a disposable cartridge (70) comprising a reservoir (80) at least partially filled with the liquid medicament and comprising a cartridge fluid coupling (90) in fluid communication with the reservoir (80), wherein the injector (60) and the cartridge (70) are releasably attachable to the housing (12) and arrestable to the housing (12) in an undeployed configuration (4), in which the injector fluid coupling (68) and the cartridge fluid
(Continued)

coupling (90) are disconnected, and wherein one of injector (60) and cartridge (70) is displaceable relative to the other one of injector (60) and cartridge (70) from the undeployed configuration (4) into the deployed configuration (6) while attached to the housing (12), wherein when in deployed configuration the injector fluid coupling (68) and the cartridge fluid coupling (90) are in fluid communication.

21 Claims, 12 Drawing Sheets

(58) Field of Classification Search
CPC .......... A61M 5/14244; A61M 5/14248; A61M 5/148; A61M 5/162
See application file for complete search history.

(56) References Cited

U.S. PATENT DOCUMENTS

| | | | | |
|---|---|---|---|---|
| 2009/0093792 | A1* | 4/2009 | Gross | A61M 5/14566 604/518 |
| 2010/0121306 | A1* | 5/2010 | Yodfat | A61B 5/14532 604/500 |
| 2012/0022496 | A1* | 1/2012 | Causey | A61M 5/14244 604/500 |
| 2013/0281928 | A1* | 10/2013 | Yodfat | A61M 5/1413 604/151 |
| 2013/0304018 | A1* | 11/2013 | Yodfat | A61B 5/14532 604/500 |
| 2014/0243786 | A1* | 8/2014 | Gilbert | A61M 37/0015 604/506 |
| 2016/0317736 | A1* | 11/2016 | Schabbach | A61M 5/14248 |

FOREIGN PATENT DOCUMENTS

| | | |
|---|---|---|
| WO | WO2006/108809 | 10/2006 |
| WO | WO2013/041702 | 3/2013 |

OTHER PUBLICATIONS

International Search Report and Written Opinion in International Application No. PCT/EP2014/078412, dated Mar. 13, 2015, 9 pages.

Rote Liste, "50. Hypophysen-, Hypothalamushormone, andere regulatorische Peptide u. ihre Hemmstoffe," Chapter 50, ed. 2008, 20 pages.

\* cited by examiner

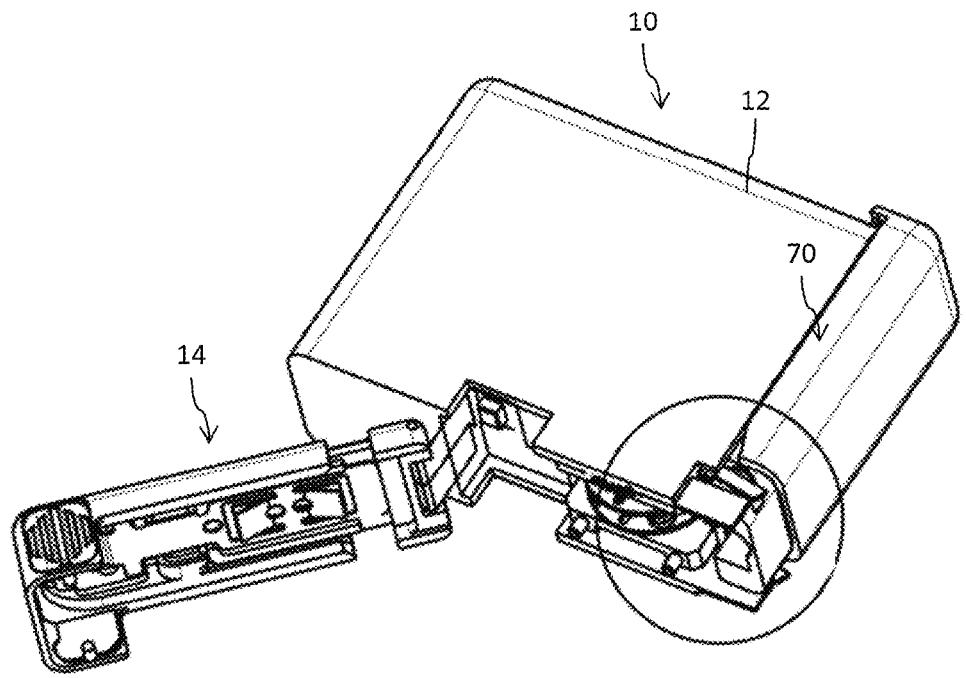
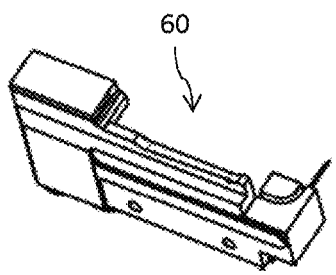
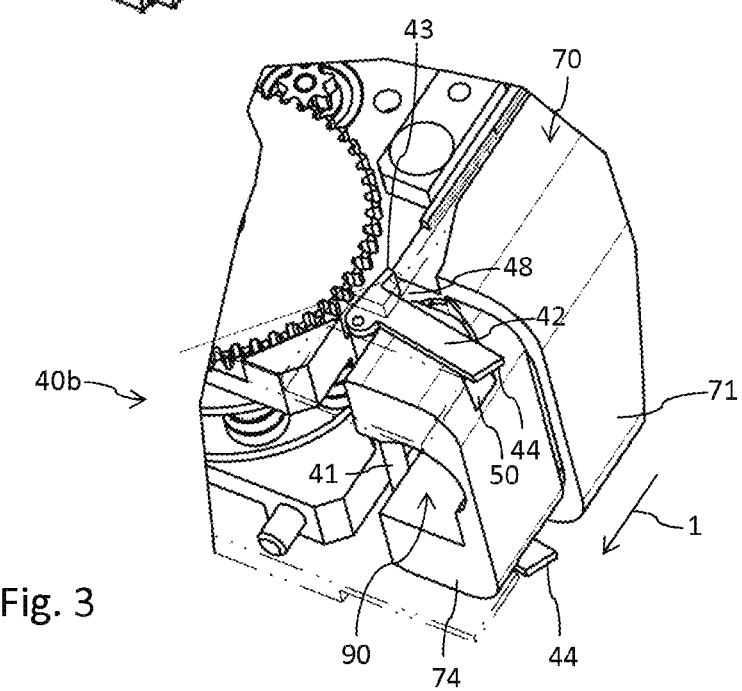
Fig. 2
Fig. 3

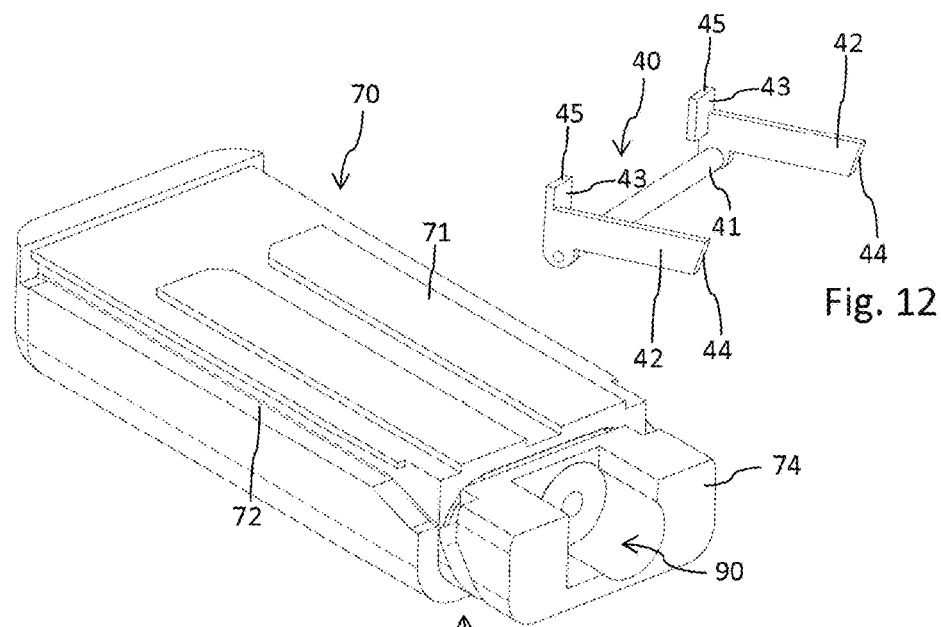
Fig. 12
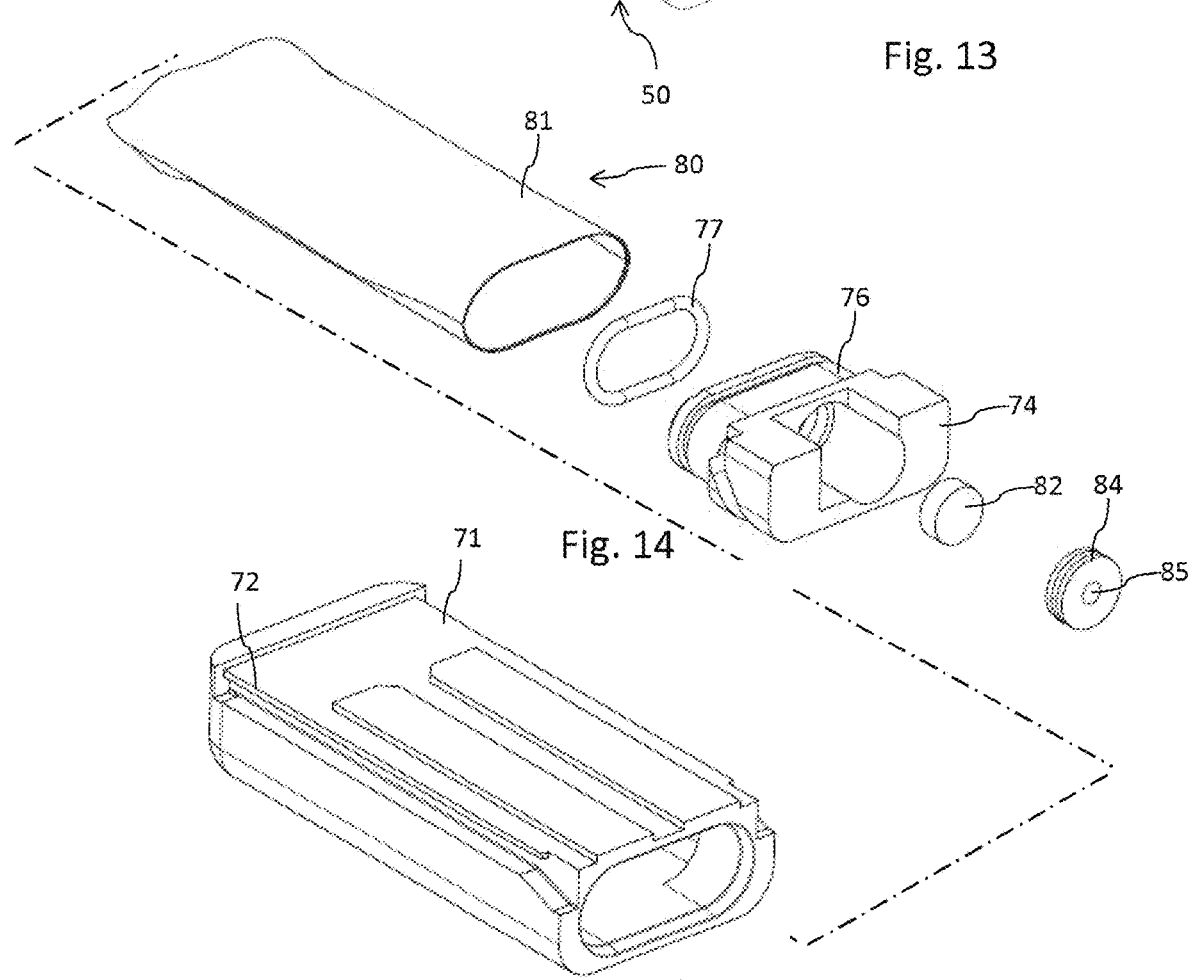
Fig. 13
Fig. 14

DRUG DELIVERY DEVICE WITH DISPOSABLE CARTRIDGE AND DISPOSABLE INJECTOR

CROSS-REFERENCE TO RELATED APPLICATIONS

This application is a U.S. national stage application under 35 USC § 371 of International Application No. PCT/EP2014/078412, filed on Dec. 18, 2014, which claims priority to European Patent Application No. 13198765.3, filed on Dec. 20, 2013, the entire contents of which are incorporated herein by reference.

FIELD OF THE INVENTION

The present invention relates to the field of drug delivery devices and in particular to the field of peristaltic pumps for controlled delivery of a medicament to a patient. In an aspect the invention relates to a drug delivery device to engage with a disposable cartridge and/or with a disposable injector.

BACKGROUND

Parenteral delivery of liquid medicaments into dermal tissue of a patient may be accomplished by administering bolus injections using a needle and a reservoir, or continuously by appropriate dispensers or transdermal patch technology which may be driven by gravity. Gravity feed systems compromise the patient's mobility and lifestyle and limit the therapy to simplistic flow rates and profiles. Ambulatory infusion pumps have been developed that provide sophisticated fluid delivery profiles accomplishing bolus requirements, continuous infusion and variable flow rate delivery.

Ambulatory pump systems typically include a reservoir containing the liquid medicament and make further use of an injection assembly comprising an injection needle and some kind of tube structure through which the medicament is transported by way of a feeder of the infusion pump.

Document WO 2013/041702 A1 discloses a peristaltic pump comprising a tube for transporting the liquid medicament, wherein the tube is arranged along a longitudinal axis. The peristaltic pump further comprises a rotatable pump head for causing a squeezing of the tube, wherein the pump head is rotatable about a rotation axis. The peristaltic pump further comprises a receptacle that is configured to receive a cartridge or a container holding the material to be transported. With peristaltic pumps featuring a pump head or feeder a rather hermetically sealed fluid path from the cartridge towards an injection needle can be provided such that the pump head or any other fluid feeding component of the peristaltic pump does not get in direct contact with the medicament. In this way, contamination of the medicament by components of the pump as well as contamination of the pump by the medicament can be effectively avoided. For reasons of hygiene as well as for patient safety and patient compliance it is of particular benefit to make use of disposable reservoirs or cartridges containing the medicament as well as to make use of disposable fluid transferring components that have to be replaced from time to time.

A fluid transferring component of such drug delivery systems providing a fluid path from a medicament reservoir towards an injection needle may be denoted as injector in the present context. For hygienic reasons as well as for patient safety and compliance it is desirable to provide a rather easy and intuitive replacement of cartridge and injector. It is a further aspect to provide a well-defined and smoothly operating fluid transferring mutual coupling of a disposable cartridge and a disposable injector. It would be rather beneficial to establish a fluid transferring coupling between injector and cartridge just immediately before the drug delivery device is initially operated so that a sealed cartridge is not prematurely or unnecessarily coupled with the injector. In this context it would be of further benefit to avoid that liquid medicament already enters the injector and its fluid transferring system, e.g. a fluid transferring tube prior to a delivery operation to be conducted by the drug delivery device.

SUMMARY OF THE INVENTION

In one aspect the invention relates to a drug delivery device for dispensing of a liquid medicament. In particular, the drug delivery device comprises a peristaltic pump but is not limited to this particular type of delivery system. The drug delivery device comprises a housing having at least one feeder member, typically in form of a rotatable pump head to engage with a fluid transporting flexible tube. The drug delivery device further comprises a disposable and replaceable injector comprising an injection needle, a flexible tube and an injector fluid coupling. The injection needle is in fluid communication with the fluid coupling via the flexible tube. The flexible tube allows for a displacement of the injection needle relative to a base of the injector. Upon activation of the drug delivery device, the injection needle may be driven out of the disposable injector and into biological tissue, in particular into and/or through dermal tissue of a patient for parenteral delivery of the liquid medicament by way of injection.

The drug delivery device further comprises as disposable cartridge comprising a reservoir at least partially filled with the liquid medicament. The disposable cartridge further comprises a cartridge fluid coupling that is in fluid communication with the reservoir. Both removable components, namely disposable injector and disposable cartridge are releasably attachable to the housing of the drug delivery device. In an attachment configuration both, the disposable injector as well as the disposable cartridge are fixable and arrestable in regard to the housing in an undeployed configuration, in which the injector fluid coupling and the cartridge fluid coupling are disconnected. In this way both disposable units, namely the disposable injector as well as the disposable cartridge can be readily attached to the drug delivery device without being in fluid communication. The mutual interaction of injector and housing as well as of cartridge and housing allows to keep at least one of disposable injector and disposable cartridge in a preassembly configuration in which the respective component is connected and attached to the drug delivery device but in which the medicament and hence the medicament reservoir is not yet subject to medicament withdrawal.

In the undeployed configuration the drug delivery device may be commercially distributed already with disposable cartridge and disposable injector readily attached thereto. In the undeployed configuration the cartridge features unabbreviated shelf life and is hence applicable and suitable for long term storage before it is handed out to end consumer or patients.

At least one of injector and cartridge is displaceable relative to the other one of injector and cartridge from the undeployed configuration into the deployed configuration while being and remaining attached to the housing. When in deployed configuration the injector fluid coupling and the cartridge fluid coupling are in fluid communication so as to provide transport of the medicament from the reservoir towards the injector, into the flexible tube of the injector and towards the injection needle. The assembly of at least one of injector and cartridge to the housing of the drug delivery device provides a displacement of the respective component relative to the other one of injector and cartridge so as to support a deployment of the drug delivery device by way of displacing one of injector and cartridge relative to the other one of injector and cartridge.

The displacement of at least one of injector and cartridge from the undeployed configuration towards the deployed configuration is typically governed and controlled by the interaction of the respective component with the housing of the drug delivery device. Hence, the deployment procedure may be controlled by the drug delivery device in a well-defined way.

According to another embodiment the drug delivery device comprises a configurable fastener to releasably fasten at least one of injector and cartridge to the housing. The configurable fastener allows to displace the at least one of injector and cartridge relative to the other one of injector and cartridge through a configuration of the device's fastener. Hence, the deployment displacement of the at least one of injector and cartridge may be controlled and governed exclusively by way of the configurable fastener of the drug delivery device. In this way, the end user is not obliged to manually manipulate the position of one of injector and cartridge in order to transfer these components into their deployed configuration. In this way, operability and handling of the device can be simplified since the user only has to operate and manipulate the configurable fastener in a predefined way rather than to take care to a rather sophisticated handling of at least one of injector and cartridge.

According to a further embodiment at least one of injector and cartridge is displaceable between an undeployed position and a deployed position by means of the fastener. Here, the fastener is configurable between a release configuration and a locking configuration. The fastener may directly engage with at least one of injector and cartridge. It is also conceivable, that the fastener engages with both of injector and cartridge to secure and to fix at least one of injector and cartridge to the housing and to displace that one of injector and cartridge relative to the other one of injector and cartridge for the purpose of establishing a deployed configuration. In the release configuration of the fastener injector and cartridge are typically in undeployed configuration. By transferring the fastener from the release configuration to the locking configuration at least one of injector and cartridge is displaced to establish the deployed configuration.

Simultaneously with the fastener-induced displacement of at least one of injector and cartridge the fastener may be also transferred from the release configuration to the locking configuration, in which the fastener itself and at least one of injector and cartridge is also disconnectably fastened to the housing of the drug delivery device. Hence, in the locking configuration, removal or replacement of any one of cartridge and injector is prevented by the fastener. In this way, the fastener provides a double function. On the one hand it provides displacement of at least one of injector and cartridge relative to the other one in order to establish and to arrive at the deployed configuration. On the other hand, transferring the fastener into the locking configuration fixes at least one of injector and cartridge to the housing or even closes a receptacle of the housing that is adapted to receive at least one of injector and cartridge.

Following another embodiment the fastener is pivotably connected to the housing between an opened configuration and a closed configuration. Here, one of injector and cartridge is attachable to the housing only when the fastener is in its opened configuration. The other one of injector and cartridge may be attachable to the housing of the drug delivery device in either configuration of the fastener. Typically, also the other one of injector and cartridge is also replaceable when the fastener is in its opened configuration.

When in closed configuration the fastener may be in engagement with both of injector and cartridge the fastener through its direct interaction with at least one of injector and cartridge and through an indirect interaction with the other one of injector and cartridge. The indirect interaction may be established by a direct mutual engagement between injector and cartridge.

According to a further aspect the other one of injector and cartridge which is not directly fastened to the housing by the fastener is displaceable from the undeployed position to the deployed position by means of transferring the fastener from the release configuration to the locking configuration. In other words, closing of the fastener may attach and fix one of injector and cartridge. Reconfiguring of the fastener when in closed configuration, e.g. from the release configuration into the locking configuration, then displaces the other one of cartridge and injector from the undeployed position to the deployed position. Here, the fastener provides a double or twofold functionality. It serves to attach and to fix one of injector and cartridge to the housing while it also provides displacement of the other one of injector and cartridge towards and into the deployed position.

According to another embodiment at least one of injector and cartridge is displaceable from the deployed position to the undeployed position by transferring the fastener from the locking configuration to the release configuration. Here, the fastener may provide a bidirectional displacement of at least one of injector and cartridge. Displacing or reconfiguring the fastener from the release configuration into the locking configuration leads to the deployed configuration. Returning the fastener from the locking configuration towards the release configuration returns the particular component, injector and/or cartridge to the disconnected undeployed configuration, in which a fluid transferring coupling of injector and cartridge is interrupted or abrogated.

In this way, reconfiguration of the fastener between the release configuration and locking configuration provides both deployment and undeployment of injector and cartridge.

According to another embodiment one of injector and cartridge, typically that one of injector and cartridge which is displaceable along the housing of the drug delivery device to transfer the undeployed configuration into the deployed configuration, comprises a linear guiding extending along a deploy direction to engage with a guide section of the housing. By providing a linear guiding or a guide section in the interface of the housing of the drug delivery device and one of injector and cartridge a well-defined linear and translational displacement of the respective component, injector or cartridge relative to the housing can be defined.

Typically, the deploy direction extends parallel to a direction of inserting or penetrating the cartridge fluid coupling. In this way and by means of displacing the cartridge relative to the injector or vice versa, along the deploy direction, the cartridge fluid coupling can be effectively coupled with the injector fluid coupling in order to obtain access to the interior of the cartridge's reservoir.

According to another embodiment the housing comprises a receptacle to receive one of injector and cartridge. In addition, the fastener is configured to releasably fix one of injector and cartridge in the receptacle. The receptacle of the drug delivery device's housing is typically closed by means of the pivotable fastener. Pivoting the fastener into the closed configuration the receptacle to receive one of injector and cartridge is effectively closed thereby securing and fixing the one of injector and cartridge to the housing. In the closed configuration the fastener is still transferable between the release and the locking configuration. While being in closed configuration and by transferring the fastener from the release configuration into the locking configuration the other one of injector and cartridge which is located outside the housing of the drug delivery device is displaceable between the deployed and the undeployed configuration to establish or to suspend a fluid communication between the cartridge and the injector.

In still another embodiment the fastener comprises a slider. Here, the fastener is transferable from the release configuration into the locking configuration by slidably displacing the slider form an extended position into a retracted position. Typically, the fastener is pivot mounted to the housing of the drug delivery device by means of a base portion to which the slider is translationally attached. Slider and base portion therefore form a kind of extendable lid to open and to close the receptacle of the drug delivery device. The slider is particularly adapted and configured to operably engage with the one of cartridge and injector that is located outside the receptacle closed by the fastener.

According to another embodiment the fastener comprises a pivotable lid with a free end formed by the slider. When in closed configuration of the fastener, the slider, which at least partially encloses one of injector and cartridge, is retractable from the extended position into the retracted position thereby displacing the other one of injector and cartridge into the deployed position. In this way, the pivotable lid formed and provided by the fastener serves to keep and to fix one of injector and cartridge to the housing while displacing the other one of injector and cartridge into the deployed configuration in which a fluid transferring coupling of injector and cartridge is established.

In a further embodiment one of injector and cartridge comprises a sliding groove to engage with a correspondingly-shaped sliding pin of the slider. When attached to the housing the sliding groove of the injector or cartridge extends at a predefined angle relative to the deploy direction along which the slider is displaceable between the extended and the retracted position. In this way and by the engagement of the at least one sliding pin in the sliding groove of injector or cartridge the respective component, injector or cartridge can be displaced in a direction perpendicular to the displacement of the slider between the extended and the retracted position. In addition the displacement of the slider with its sliding pin in engagement with the sliding groove of one of injector or cartridge may provide a locking mechanism for the slider and hence for the fastener itself.

According to another embodiment the drug delivery device further comprises a stopper which is pivotably arranged at the housing between a release configuration and a stop configuration. The stopper is particularly adapted to inhibit displacement of one of injector and cartridge beyond the undeployed position towards the deployed position. The stopper effectively serves and prevents premature deployment of cartridge and injector upon assembly of cartridge and injector to the drug delivery device's housing. Here, the component of injector and cartridge which is to be displaced into the deployed configuration through interaction with the fastener typically engages with the pivotable stopper at the housing.

It is particularly intended, that the stopper is pivoted into the release configuration by interaction with the fastener, in particular through an interaction of the fastener's slider and/or by means of the sliding pins of the slider. It is generally conceivable, that the stopper is pivoted into the release configuration when the fastener reaches the closed configuration. Alternatively it is conceivable, that the stopper is pivoted into the release configuration when the slider is initially transferred from the release configuration into the locked configuration, while the fastener is in closed configuration. Displacement of the stopper into the release configuration is required in order to displace the respective component, injector or cartridge from the undeployed configuration into the deployed configuration or deployed position. It is generally conceivable, that the stopper is engaged with a return element, such like a return spring generally serving to keep the stopper in the stop configuration by default.

The stopper provides an interlock mechanism that serves to prevent manual displacement of at least one of injector and cartridge into a deployed position or deployed configuration. In this way, an accidental or unintentional premature deployment of cartridge and injector can be effectively prevented.

According to a further embodiment the sliding pin is engageable with the stopper by transferring the fastener into the closed configuration in which the sliding pin is configured to pivot the stopper into the release configuration by displacing the slider towards the retracted position. Hence, due to a pivoting of the fastener into the closed configuration the sliding pin may already engage with the stopper for displacing or rotating the stopper into the release configuration. In addition or alternative it is conceivable, that it is only due to the sliding displacement of the slider towards the retracted position that the sliding pin engages with the stopper to pivot the stopper into and towards the release configuration.

In still another embodiment the fastener is lockable to the housing by means of the slider's sliding pin engaging with a sliding groove's locking portion that extends substantially perpendicular to the deploy direction. Typically, when in closed configuration, hence when closing the housing's receptacle, the slider is displaceable between the extended and retracted positions in a direction perpendicular to the deploy direction, hence parallel to the locking portion of the sliding groove. In this way, a holding force can be transferred and provided by the mutual engagement of slider and the sliding groove's locking portion, which force acts substantially parallel to the deploy direction.

It is of particular benefit, when cartridge and injector form or contribute to a lateral sidewall portion of the drug delivery device's housing. In this way, cartridge and injector may engage in a corner section of the housing which may be covered by a free end of the pivotable fastener. Assuming that it is the injector that is insertable into the receptacle to be closed by the fastener it is then the cartridge which is displaceable along and relative to the housing between the undeployed configuration and the deployed configuration under the effect of the fastener's slider.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group-Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference numerals used in the appended claims are not to be construed as limiting the scope of the invention.

BRIEF DESCRIPTION OF THE DRAWINGS

In the following an embodiment of the disposable delivery assembly in connection with a drug delivery device is described in more detail by making reference to the drawings, in which:

FIG. 2 shows the cartridge assembled to the drug delivery device while the injector is still disassembled, FIG. 3 shows an enlarged view of a section of the drug delivery device according to FIG. 2, FIG. 12 shows an isolated view of the pivotable stopper, FIG. 13 is a perspective view of the cartridge, FIG. 14 is an exploded view of the cartridge according to FIG. 13.

DETAILED DESCRIPTION

Figure 1:
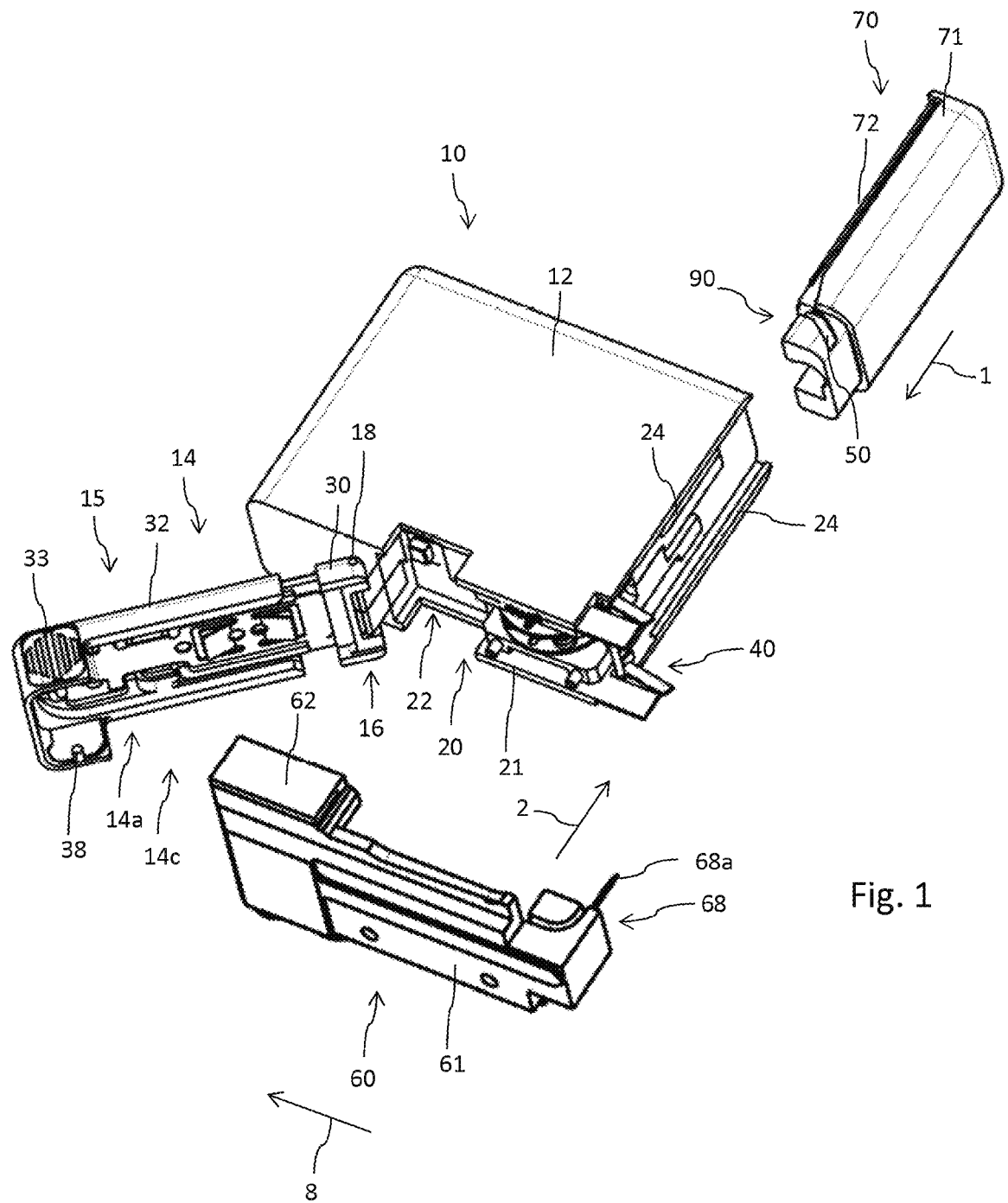
FIG. 1 shows the drug delivery device with disassembled disposable cartridge and disposable injector.
Figure 4:
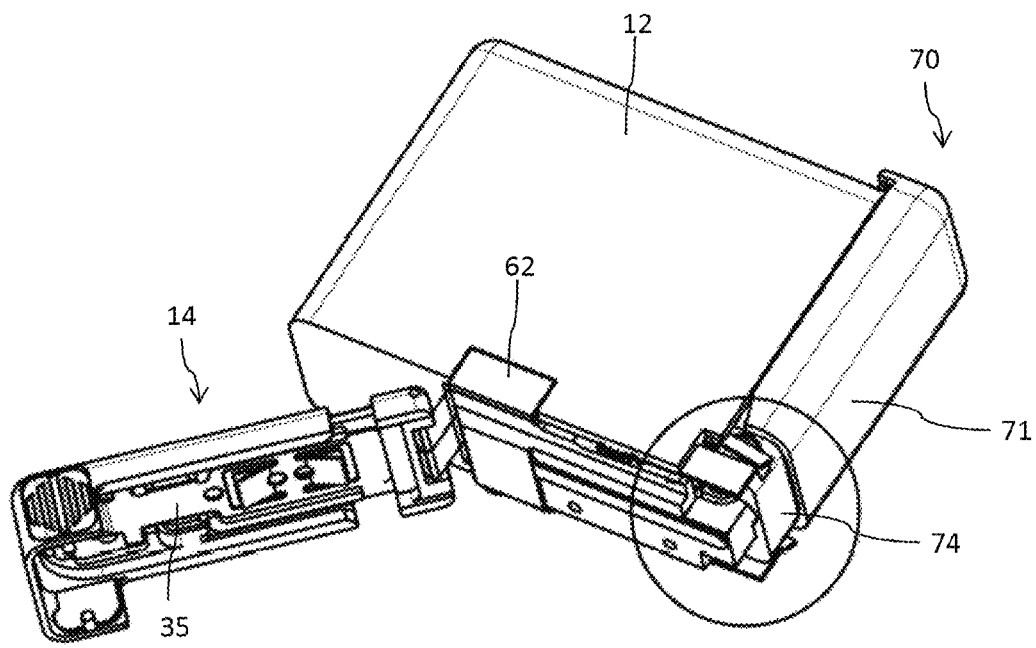
FIG. 4 shows the drug delivery device according to FIG. 2 with the injector assembled in a housing of the drug delivery device.

The drug delivery device 10 as it is illustrated in FIGS. 1-4 comprises a housing 10 featuring a receptacle 20 which is closeable by a fastener 14 that serves as a lid 15 for the receptacle 20.

Figure 6:
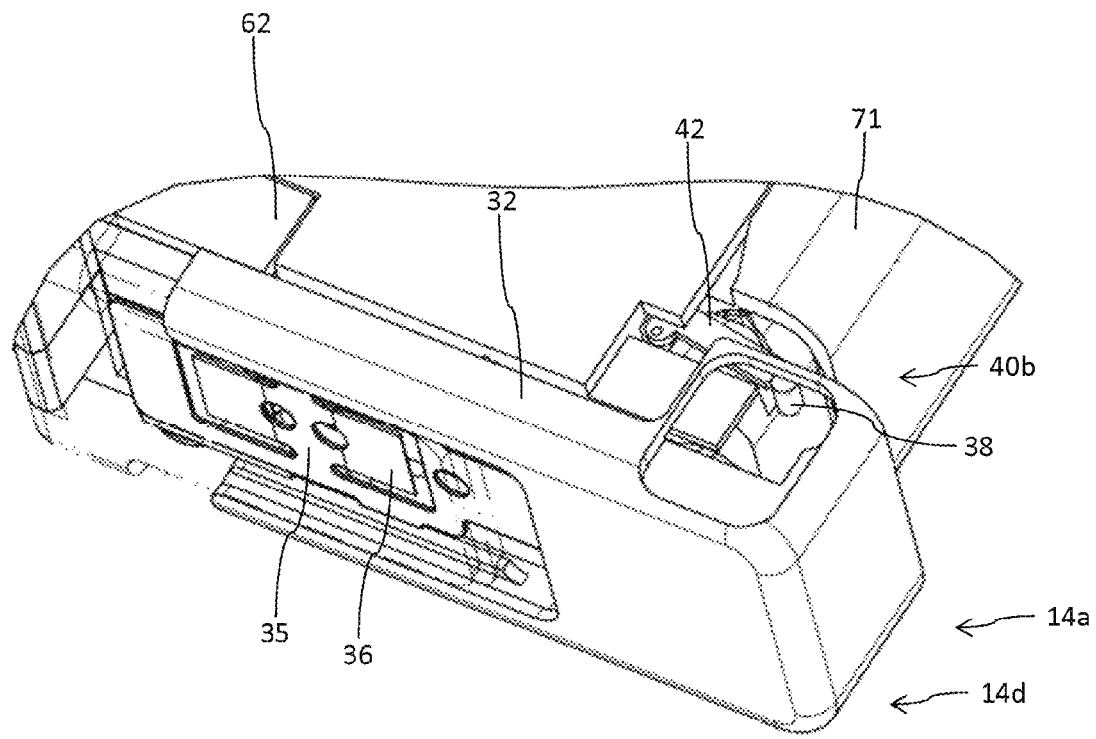
FIG. 6 shows the configuration according to FIG. 5 with the fastener in closed but extended configuration.

The fastener 14 is pivot mounted to the housing 12 by means of a hinge 16. Consequently, the fastener 14 is pivotable between a closed configuration 14d as shown in FIG. 6 and an opened configuration 14c as illustrated in FIG. 1 for instance. In the opened configuration 14c, the receptacle 20 is accessible from outside to insert a disposable injector 60 as for instance illustrated in FIGS. 10 to 11b. The injector 60 is insertable into the receptacle 20 along an insert direction 2 as illustrated in FIG. 1.

Figure 10:
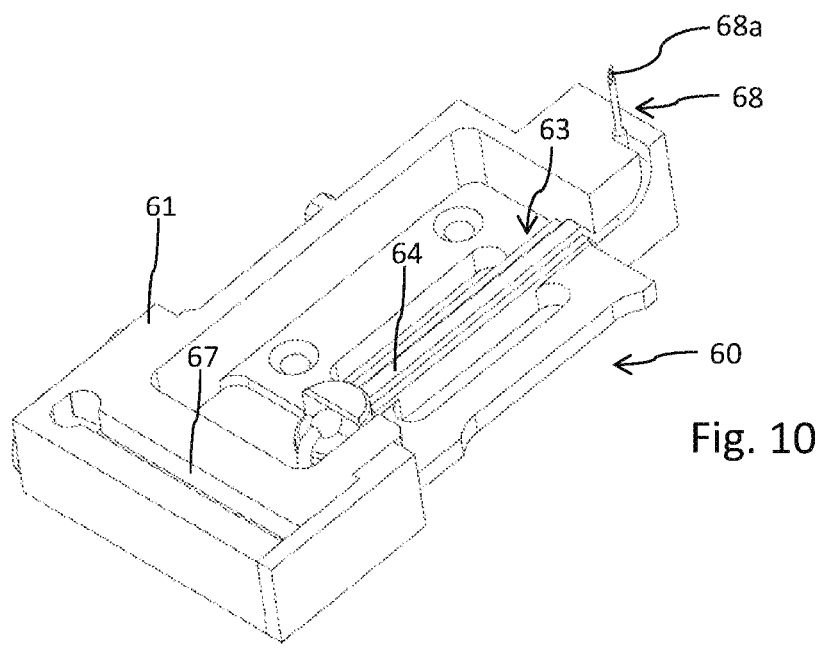
FIG. 10 shows a perspective view of the injector.

The drug delivery device 10, typically implemented as a peristaltic pump, is designed to releasably engage with a disposable injector 60 and with a disposable cartridge 70. The disposable injector 60 as shown in FIG. 10 comprises a base 61. The base features a track 63 through which a flexible tube 64 is guided. In the region of the track 63 the feeder member 100 or the pump head of the drug delivery device 10 engages with the flexible tube 64. Here, the flexible tube 64 is squeezed by the feeder member 100 in order to transport the liquid medicament from the reservoir 80 of the cartridge 70 towards an injection needle 65 of the injector 60.

Figure 11A:
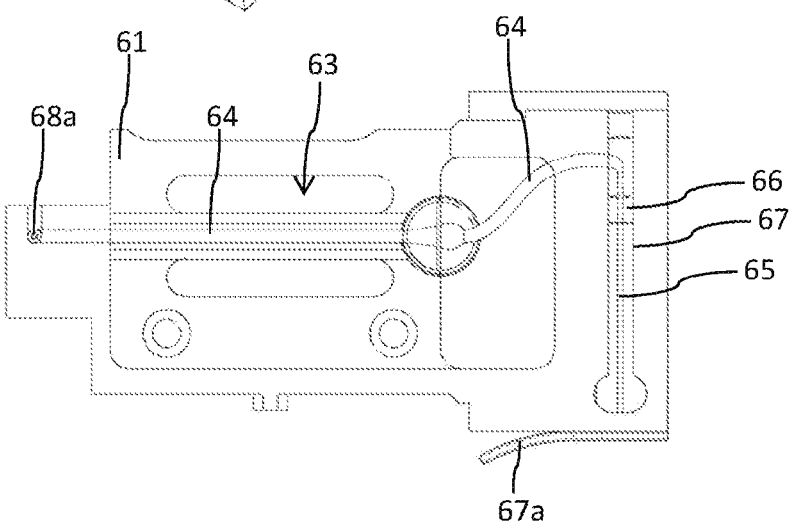
FIG. 11a shows the injector according to FIG. 10 in a top view with a retracted injection needle and FIG. 11b shows the injector according to FIG. 10 with the injection needle in extended position.
Figure 11B:
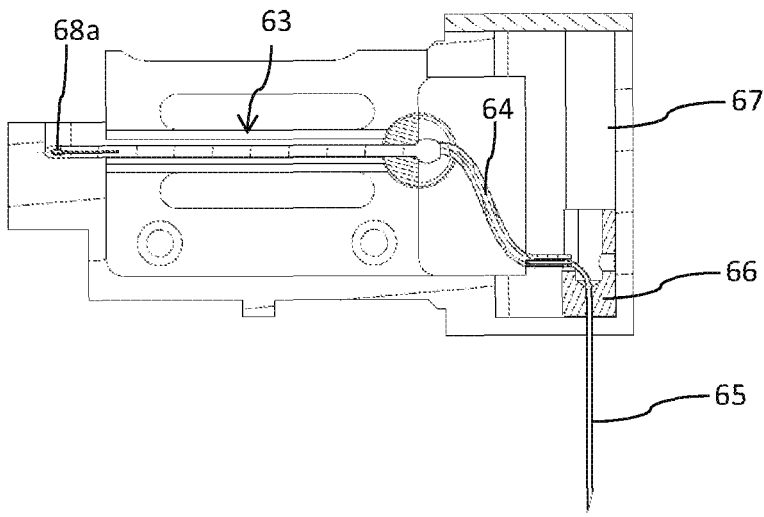
Figure 15:
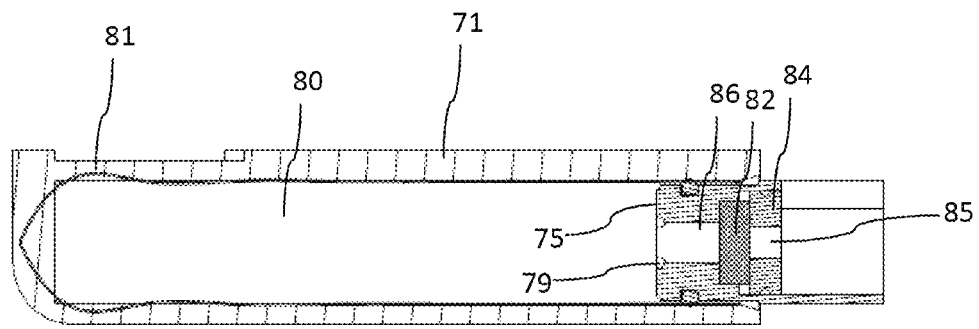
FIG. 15 shows the cartridge in longitudinal cross-section, FIG. 16 schematically shows an enlarged view of the cartridge's base.

The injection needle 65 is also a component of the injector 60. As can be seen from a comparison of FIGS. 11a and 11b, the injection needle 65 is attached to a piston 66, which is slideably received in a conduct 67. An outlet of the conduct 67 is covered by a protector 67a as shown in FIG. 11a. Upon activation of the injector 60 the protector 67a typically in form of an adhesive foil is to be removed, hence allowing the piston 66 to slide along the conduct 67 thereby advancing the injection needle 65 into an extended position as illustrated in FIG. 11b.

Typically, when arranged in the receptacle 20 of the drug delivery device 10 that side face of the injector 60 featuring the outlet for the injection needle 65 forms an integral component of the outer surface or housing 12 of the drug delivery device 10. In typical application scenarios, the drug delivery device 10 is e.g. adhesively attached to the skin of a patient. Upon activation of the injector 60, hence upon activation of the drug delivery device 10 the injection needle 65 is automatically positioned into the extended position thereby piercing or penetrating dermal tissue for transdermal or subcutaneous injection of the liquid medicament.

Opposite the injection needle 65 the injector 60 comprises an injector fluid coupling 68, presently in form of a hollow but tipped cannula 68a. As becomes apparent from FIG. 10, the injector fluid coupling 68 extends from a sidewall of the injector's base 61. The tipped injector fluid coupling 68 serves to penetrate and to pierce a cartridge fluid coupling 90 of the cartridge 70 as for instance illustrated in FIG. 13. The cartridge fluid coupling 90 comprises a pierceable seal 82, typically in form of a sealing disc. The pierceable seal 82 closes a fluid channel 86 which is in fluid communication with the interior of a reservoir 80 containing the liquid medicament. The reservoir 80 comprises a flexible bag 81 which allows and supports a suction-based withdrawal of a medicament therefrom. The outlet of the fluid channel 86 is closed by the pierceable seal 82, which is secured within an opening of a base of the cartridge 70 by means of an insert 84. The insert 84 comprises a central through opening 85 which allows to receive the tipped injector fluid coupling 68, hence the cannula 68a. The pierceable seal 82 typically serves as a septum of elastic material, which may even be pierced multiple times without exhibiting substantial leakage.

The cartridge 70 features a base 74 having and forming a fluid channel 86 and further has a housing 71 providing a protective sheath for the flexible bag 81 forming the reservoir 80 for the liquid medicament.

The base 74 further comprises a socket 76 extending from a planar surface of the base 74. The socket 76 extends into the flexible bag 81 so as to close an opening of the flexible bag. In addition and in order to seal the interconnection of flexible bag 81 and the socket 76, the socket comprises an annular or surrounding groove 78 at its outer circumference. In addition and as becomes apparent from FIG. 12, the housing 71 features a receptacle to engage with the socket 76 in a press fit. Here, the housing 71 extends over and all around the socket 76 and an O-ring 77 located in the socket's groove 78, thereby squeezing and fixing the flexible bag 81 therebetween.

In this way, a sealed interconnection of socket 76 and flexible bag 81 can be provided without any adhesives and without application of thermal energy. By having a press fit arrangement of the flexible bag 81 with the socket 76 a rather medicament friendly seal can be provided.

The outlet section forming the cartridge fluid coupling 90 is arranged and oriented substantially parallel to the fluid channel 86 which is in extension of the reservoir 80 and parallel to a linear guiding 72 as will be explained below. In this way, the pierceable seal 82 can be pierced and penetrated by the injector fluid coupling 68, hence by its cannula 68*a*. The insert 84 that keeps the pierceable seal 82 in position may comprise an outer thread to engage with an inner thread of a corresponding opening of the base 74. Alternatively, the insert is press fitted or squeezed in the base 74.

Figure 16:
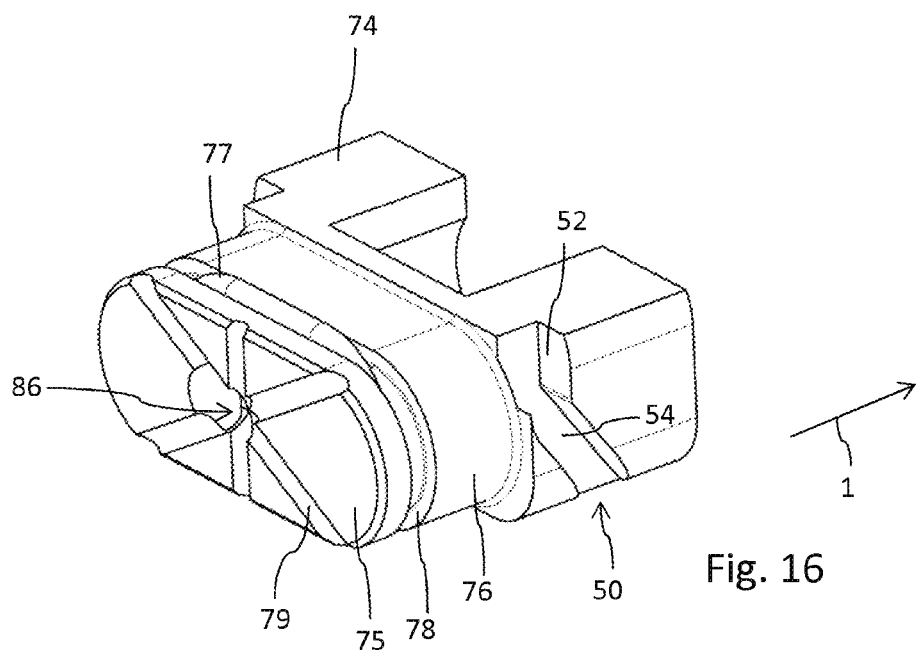
Figure 17:
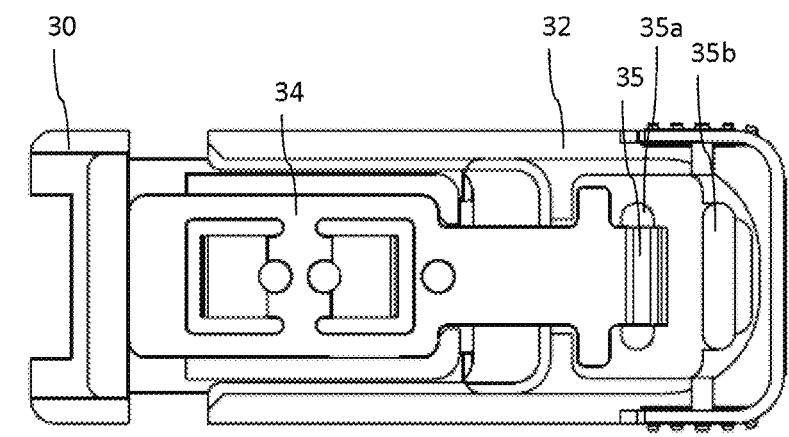
FIG. 17 shows the fastener in the extended configuration.
Figure 18:
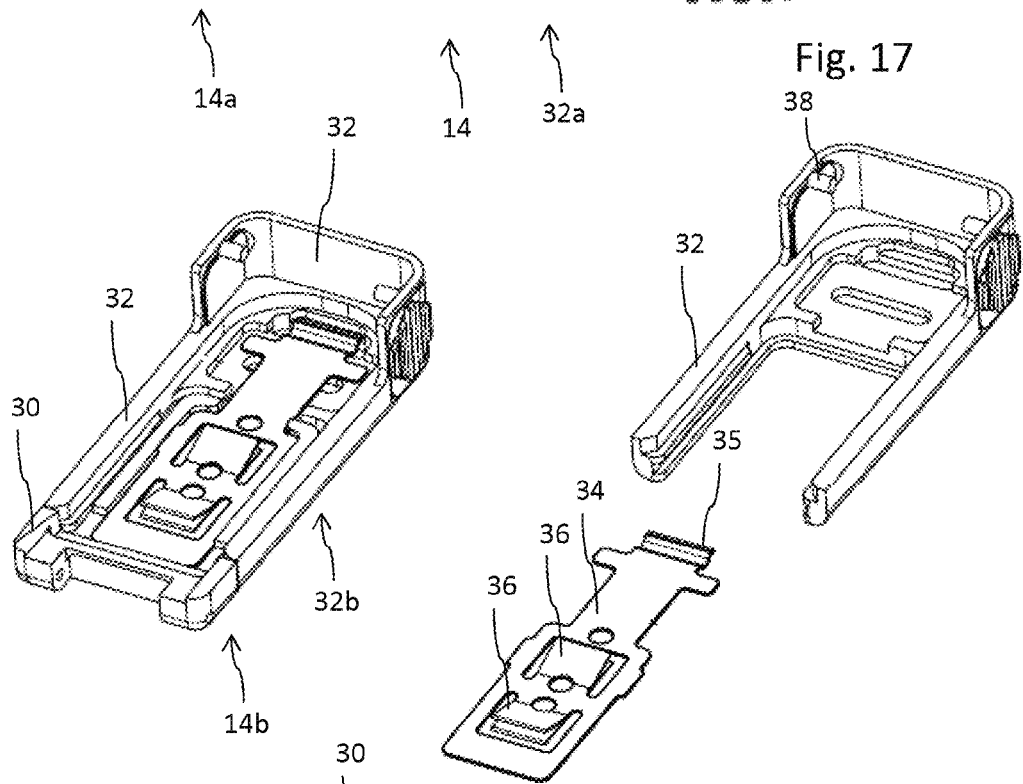
FIG. 18 shows a perspective view of the fastener with a slider in the retracted position.

As it is further illustrated in FIG. 16 the front face 75 of the socket 76 comprises several grooves 79 that extend across the front face 75 towards the outer circumference or to the outer edge thereof. All these grooves 79 merge with the central fluid channel 86. Since the flexible bag 81 is of flexible material it is conceivable that a portion thereof may get in abutment with a portion of the front face 75 when extracting the liquid medicament from the reservoir 80. Here, the grooves 79 provide a respectable fluid flow even in case that the portion of the front face 75 coinciding with the fluid channel 86 should be obstructed or should get in abutment with an inside-facing portion of the flexible bag 81.

As becomes apparent from FIGS. 1 and 2 disposable injector 60 and disposable cartridge 70 are separately releasably engageable with the housing 12 of the drug delivery device 10. For this purpose the cartridge 70 comprises a linear guiding 72, e.g. in form of a longitudinal groove at its longitudinally extending housing 71 that engages with a correspondingly-shaped guide section 24 at a sidewall portion of the housing 12 as illustrated in FIG. 1. By means of the linear guiding 72 of the cartridge 70 engaging with the housing's guide section 24, the cartridge 70 is displaceable along the housing 12 of the drug delivery device along a deploy direction 1.

The injector 60 extends substantially perpendicular to the elongation of the cartridge 70 and is configured to be positioned in a receptacle 20 located at an adjacent sidewall portion of the drug delivery device's 10 housing 12. The injector 60 having a base 61 features a mating structure 62 that mates with a recessed structure 22 of the housing 20, hence of a sidewall portion 21 of said housing 20. In this way, the mating structure 62 may be flush mounted to the outside facing portion of the housing 12. The mating structure 62 of the injector 60 may form a component of the housing 12 and may contribute to the outer appearance of the drug delivery device 10 as becomes apparent from FIG. 4 for instance. In this way, the injection needle 65 may be driven in the extended position as illustrated in FIG. 11*b*, thereby protruding from the substantially planar-shaped housing 12 of the drug delivery device 10, wherein a plane shaped housing portion of the drug delivery device 10 may be equipped or furnished with an adhesive to attach the drug delivery device 10 to a body portion of a patient.

As it is apparent from FIG. 1, the injector fluid coupling 68 in form of a tipped cannula 68*a* extends substantially perpendicular to the elongation of the injector 60. In particular, the injector fluid coupling 68 and its tipped cannula 68*a* extend in deploy direction 1 so as to engage with the cartridge fluid coupling 90 of the cartridge.

Figure 7:
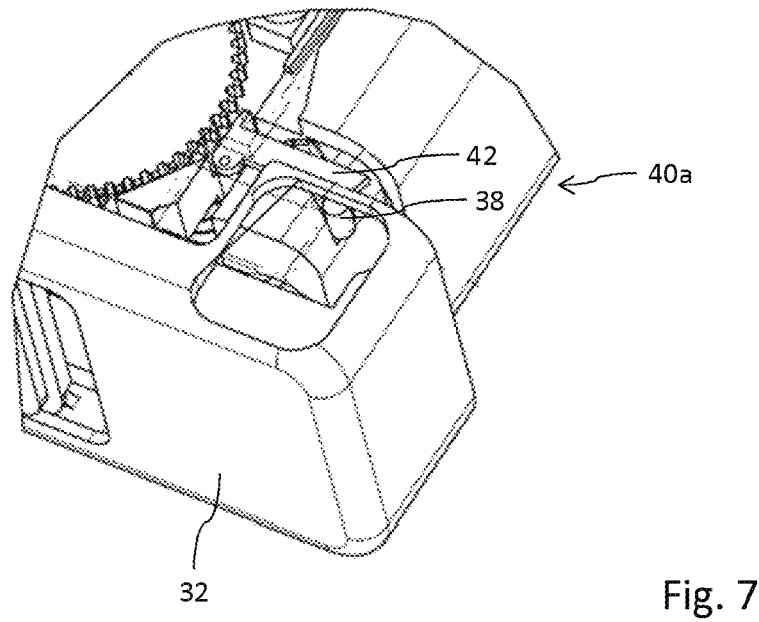
FIG. 7 shows the slider of the fastener in an intermediate position at the beginning of transferring the fastener from a release configuration into a locking configuration.
Figure 8:
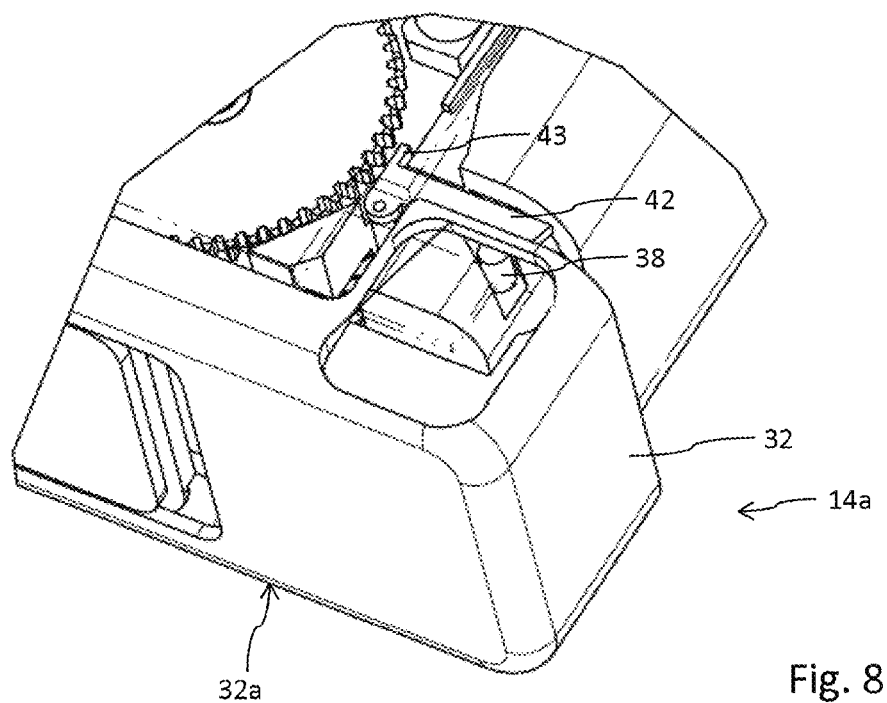
FIG. 8 shows the slider of the fastener further positioned in direction to the locking configuration and FIG. 9 shows the fastener in locking configuration.
Figure 9:
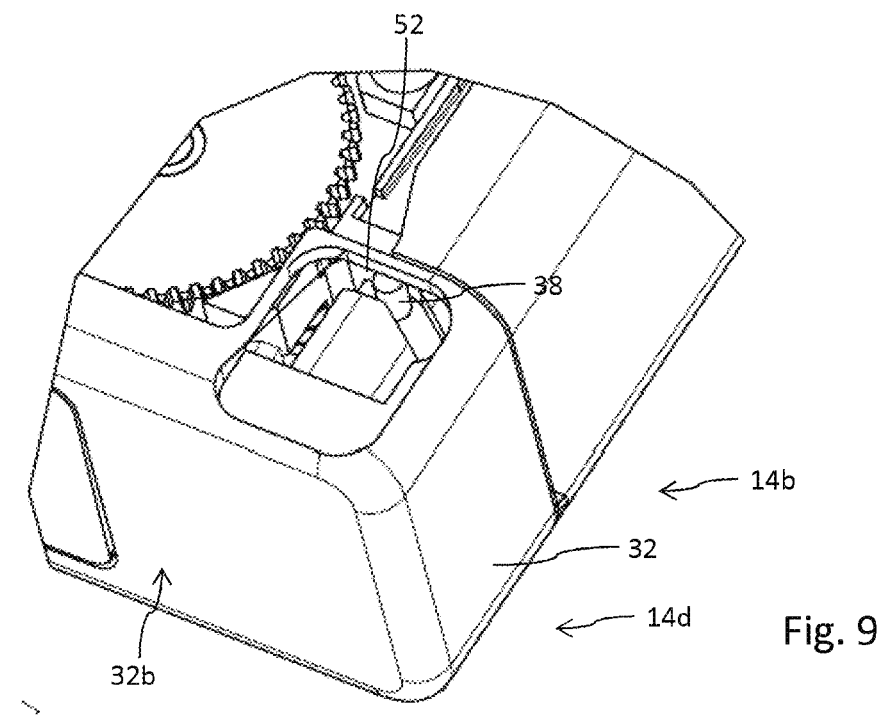

The cartridge 70 is attachable and displaceable along the deploy direction 1 along the side face of the housing 12 being equipped with the guide sections 24. Here, the cartridge 70 is displaceable in deploy direction 1 until it engages with a pivotable stopper 40 which is shown in an isolated view in FIG. 12 and whose interaction with the cartridge 70 is shown in detail in FIG. 3. The pivotable stopper 40 is pivotable between a stop configuration 40*b* as indicated in FIG. 3 and a release configuration 40*a* as shown in FIG. 7. In the stop configuration 40*b* a stop portion 43 of the stopper 40 directly abuts with a stop face 48 of the housing 71 of the cartridge 70 which stop face is for instance shown in FIGS. 13 and 14. The stopper 40 is pivotable with regard to an axis 41 extending between two legs 42 that are oriented parallel to each other and that are unitary formed with the axis 41 and with respective stop portions. The free ends of the stop portions 43 featuring a stop face 45 extend substantially perpendicular to the elongation of the legs 42. A free end of the legs facing away from the axis 41 is provided with a beveled portion or with a beveled end 44 to engage and to cooperate with inwardly extending guiding pins 38 of the fastener 14 as will be explained below.

In the configuration as shown in FIGS. 2 and 3 a displacement of the cartridge 70 along the deploy direction 1 is limited by the cartridge's stop face 48 engaging and abutting with the stop portion 43 extending substantially in deploy direction 1. Further displacement of the cartridge 70 in deploy direction and in order to establish a fluid communication between the cartridge 70 and the injector 60 requires pivoting of the stopper 40 in a counter-clockwise direction in the illustration according to FIG. 3. Such a pivoting may be induced by closing of the fastener 14 hence by pivoting the fastener 14 into a closed configuration 14*d* as for instance shown in FIG. 22.

Figure 24:
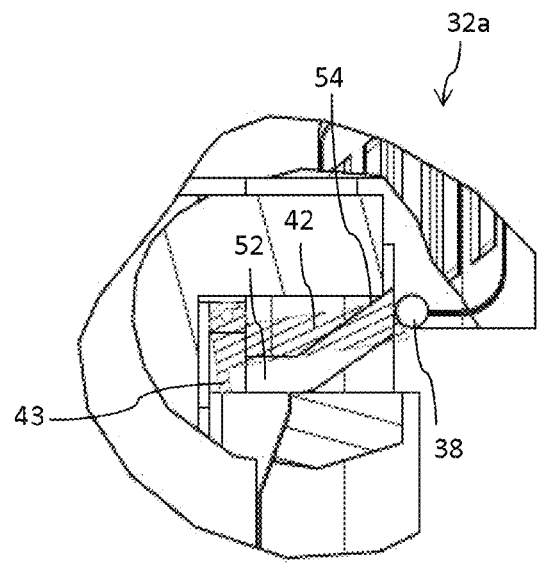
FIG. 24 shows an enlarged view of the sliding pin in engagement with the stopper in the configuration according to FIG. 22
Figure 25:
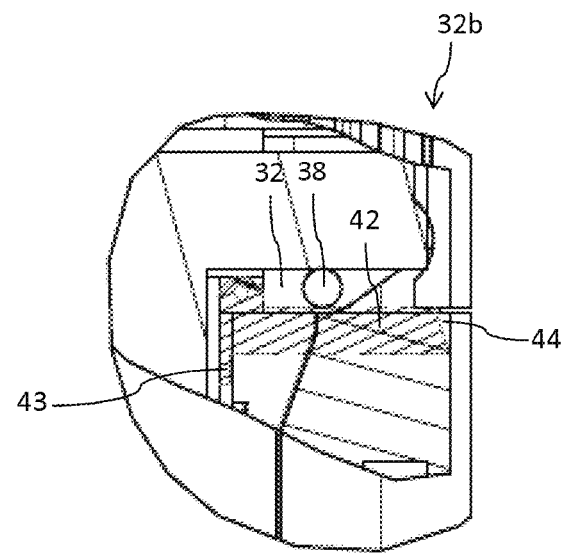
FIG. 25 shows the position of the sliding pin in the sliding groove's locking portion when cartridge and injector are in deployed configuration.

In the closed configuration 14*d* the inwardly extending guiding pins 38 located at an inside portion of the fastener 14 engage with the beveled ends 44 of the stopper as shown in detail in FIG. 24. Typically, the guiding pins 38 extend inwardly from a slider 32 of the fastener 14, which slider 32 being slidably fastened to a base portion 30 of the fastener 14 and which base portion 30 being pivotably attached to the housing 12. Engagement of the guiding pins 38 with the stopper 40 may already take place when the fastener 14 reaches the closed configuration 14*d*, in which the receptacle 20 receiving the injector 60 is substantially closed by the lid-like fastener 14. In another configuration and as shown in detail in FIG. 24, upon reaching of the closed configuration 14*d* the guiding pins 38 may just get in contact with the beveled ends 44 of the stopper 40 without inducing a momentum thereto. It is then only due to a retraction of the fastener 14, in particular of a slider 32 forming a free end of the fastener 14 towards the locking configuration 14*b* that the stopper 40 is rotated counter-clockwise in the illustration according to FIG. 3 or clockwise in the illustration according to FIG. 24 thereby displacing the stop portion 43 of the stopper 40 out of engagement with the stop face 48 of the cartridge.

Figure 22:
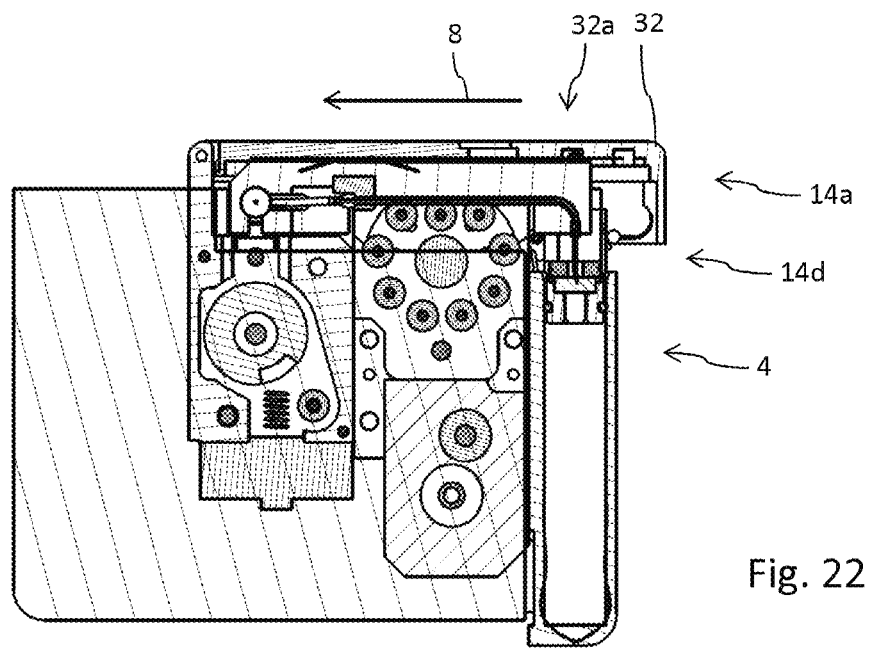
FIG. 22 shows the drug delivery device according to FIG. 21 with the fastener in closed but released configuration and FIG. 23 shows the drug delivery device with the fastener in closed and locking configuration and hence with cartridge and injector in deployed configuration.
Figure 23:
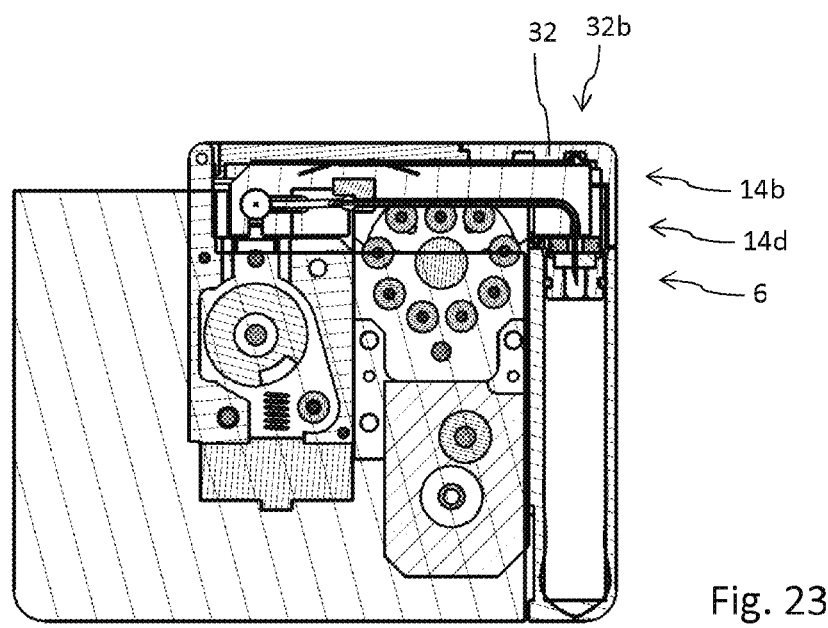

As illustrated further the base 74 of the cartridge 70 comprises a sliding groove 50 serving as a coulisse for the guiding pins 38 of the fastener 14. According to FIG. 16, the sliding groove 50 comprises a beveled portion 54 extending at a particular angle with regard to the deploy direction 1. The beveled portion 54 then merges into a substantially vertically extending locking portion 52 which extends substantially perpendicular to the deploy direction 1 but substantially parallel to a displacement direction 8 along which a portion of the fastener 14, in particular a slider 32 is displaceable between an extended position 32a as shown in FIG. 22 and a retracted position 32b as shown in FIG. 23.

Figure 5:
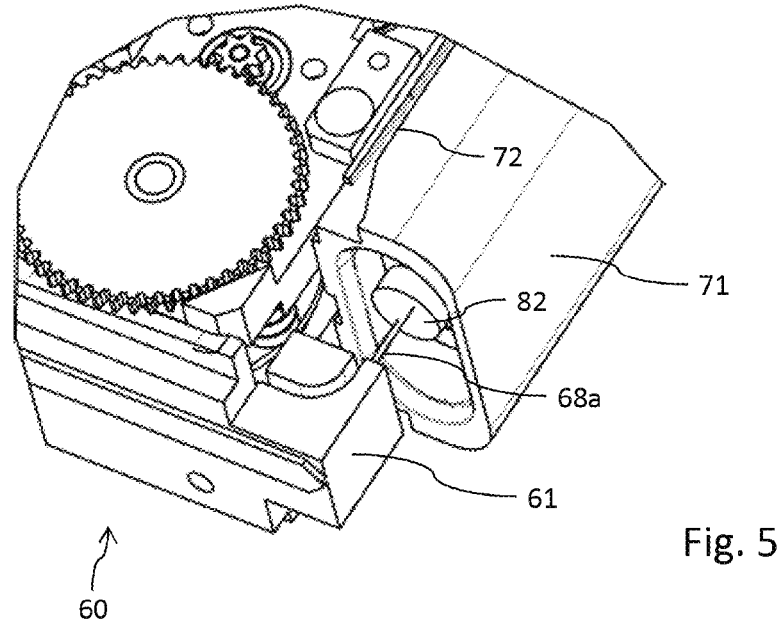
FIG. 5 shows an enlarged view of an undeployed coupling of cartridge and injector.

As it is apparent from FIG. 1, the beveled portion 54 of the sliding groove 50 of the cartridge's 70 base 74 extends towards the deploy direction 1 in opposite direction to the locking direction 8. In the undeployed configuration as shown in FIGS. 5 and 6 the guiding pins 38 are in a position just to enter the beveled portion 54 of the sliding groove 50 that faces away from the locking portion 52. As it becomes further apparent from FIG. 3, the entry of the beveled portion 54 substantially coincides with the beveled ends 44 of the legs 42 of the pivotable stopper 40.

Upon entering the sliding groove 50 by a displacement of the fastener 14, hence by a displacement of the fastener's 14 slider 32 in locking direction 8, an initial displacement of the guiding pins 38 in locking direction 8 initially serves to pivot the stopper 40 towards the release configuration 40a as shown in FIG. 7. Thereafter, a further sliding displacement of the guiding pins 38 in locking direction 8 leads to a forced advancing of the guiding pins 38 along the beveled portion 54 of the sliding groove 50 until the guiding pins 38 reach the locking portion 52 thereof extending substantially parallel to the locking direction 8.

Once the medicament contained in the reservoir 80 has been withdrawn thus requiring a replacement of the cartridge 70 the slider 32 may be displaced in a direction opposite to the locking direction 8, typically by means of the ripples 33 provided at the outer surface of the free end of the slider 32. Since the guiding pins 38 remain in permanent engagement with the sliding groove 50 of the cartridge's 70 base 74, a reverse displacement of the slider 32 of the fastener 14 into the release configuration 14a also leads to a reverse motion and displacement of the cartridge 70 in a direction opposite the deploy direction 1.

With the present embodiment it is of particular benefit, that the fastener 14 with its slider 32 serves as a lid 15 to cover and to close the receptacle 20 of the drug delivery device 10 in which the injector 60 is releasably received. Interlocking of the slider 32 and hence of the fastener 14 is obtained through the interaction of the guiding pins 38 of the slider 32 with the sliding groove 50 of the cartridge 70. In the closed configuration 14d and in the locking configuration 14b as for instance shown in FIG. 23, the slider 32 and hence the fastener 14 is interlocked with and to the housing 12 in the locking configuration 14b through its guiding pin's 38 interaction with the sliding groove's 50 locking portion 52 of the cartridge 70.

The fastener 14 not only provides a twofold function by fixing the injector 60 to the housing 12 and by displacing the cartridge 70 between the undeployed configuration 4 and the deployed configuration 6 but through its interaction with the sliding groove 50 also serves to lock the fastener 14 and hence the lid 15 in the locking configuration 14d, in which the slider 32 is substantially flush with the housing 71 of the cartridge as illustrated in FIG. 23. Here, as soon as either the housing 71 of the cartridge 70 may extend or protrude from an adjacent housing portion 12 or in the event that the slider 32 extends or protrudes from the outer circumference of the adjacently located cartridge housing 71 a clear and unequivocal indication is given to a user, that the drug delivery device 10 is not correctly assembled or that the drug delivery device is currently under maintenance. In this way, a haptic feedback can be given to a user, whether cartridge 70 and injector 60 are correctly mounted to the housing 12.

Deployment of injector 60 and cartridge 70, hence establishing of a fluid transferring interconnection of injector 60 and cartridge 70 may only take place through interaction with the fastener 14 of the drug delivery device 10. In a reverse order also a disconnecting and decoupling of disposable cartridge 70 and disposable injector 60 can be provided simply by opening of the lid 15. For this the interlock between the fastener 14 and the cartridge has to be suspended by means of shifting the slider 32 from the locking configuration 14b towards the release configuration 14a. Here, the engagement of the sliding groove 50 with the guiding pins 38 induces a displacement of the cartridge 60 towards its undeployed position 4, hence in a direction opposite the deploy direction 1. Once the guiding pins 38 leave the sliding groove 50 the fastener 14 will be automatically lifted by a predefined angle due to the wings 36 of the spring 34 applying pressure to the upper surface of the injector 60 as will be explained below. This is a clear indication to the user, that the drug delivery device 10 is in a maintenance mode.

Due to the automated disconnection of cartridge 70 and injector 60 upon or prior to an opening of the lid 15 contamination of the environment by droplets of the medicament rinsing out of the injection needle 65 can be effectively avoided. Also here, it is conceivable that cartridge 70 and injector 60 comprises mutually corresponding tamper proof members, which serve to avoid reconnection or redeployment of cartridge 70 and injector 60 once they have been transferred from the deployed configuration 6 back into the undeployed configuration 4.

Figure 20:
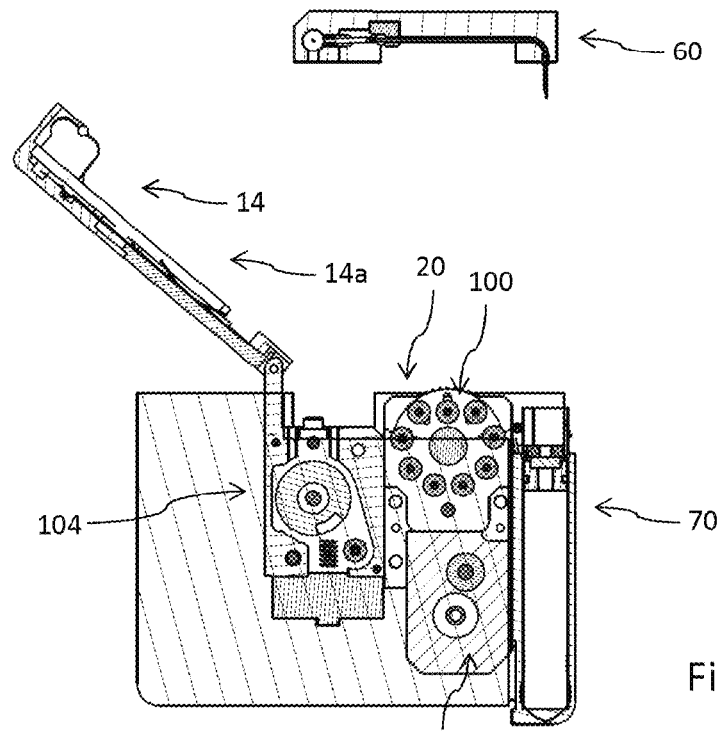
FIG. 20 shows the drug delivery device in an initial configuration prior to assembly of the injector.

The drug delivery device 10 as for instance illustrated in FIG. 20 is designed and implemented as a peristaltic pump. It comprises a feeder member 100, presently in form of a rotatable pump head that engages with the flexible tube 64 in order to squeeze the same for drug delivery. In addition, the drug delivery device 10 comprises an energy source, typically in form of an electric battery (not illustrated). Moreover, it comprises an injection drive 104 by way of which the injection needle 65 can be displaced along the conduct 67. By means of the injection drive 104 the injection needle 65 can be displaced from an initial position into an extended position as shown in FIG. 11b. In the same way the injection drive 104 may serve to retract the extended injection needle 65. Additionally, the peristaltic pump 10 comprises a delivery drive 106 in order to set the pump head, hence the feeder member 100 in rotation during and for drug delivery.

The pivotable fastener 14 comprises two portions, namely a base portion 30 by way of which the fastener 14 is pivotably attached to the housing 12 via a hinge 16. Attached to the base portion 30 the fastener 14 comprises a slider 32 forming a free end of the fastener 14 effectively providing a lid 15.

Figure 19:
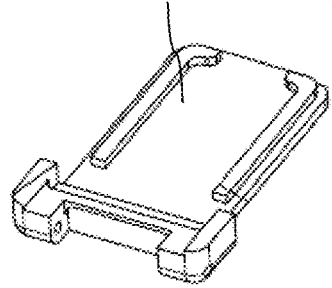
FIG. 19 shows an exploded view of the various components of the fastener.
Figure 21:
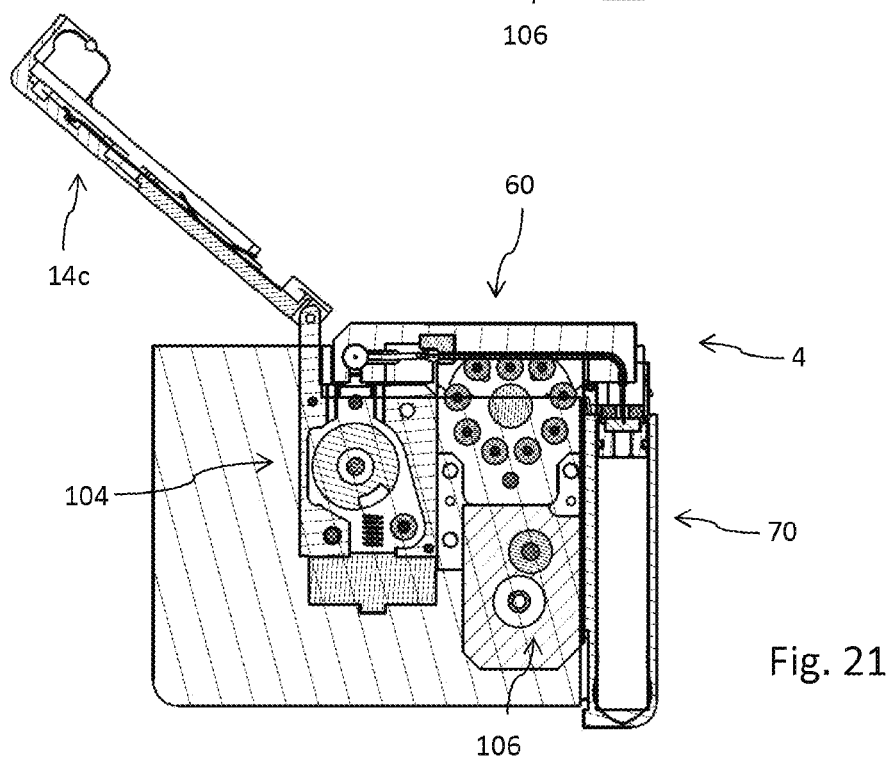
FIG. 21 shows a side view of the drug delivery device with the injector assembled to the housing of the drug delivery device while the cartridge is in an undeployed position.

The slider 32 and the base portion 30 are interconnected by means of a planar spring 34 as shown in FIG. 19. The spring 34 comprises a latch portion 35 to engage with two recesses 35a, 35b at an inside-facing portion of the slider 32. By way of the latch portion 35 engaging with either a distal recess 35b or with a proximal recess 35a, as indicated in FIGS. 22 and 23 the radial position of the slider 32 with regard to the base portion 30 and in regard to the hinge 16 and the pivot axis 18 can be modified. By means of the spring 34 and its latch portion 35 the slider 32 can be transferred from an extended configuration as shown in FIG. 21 into a retracted position 32b as shown in FIG. 20.

By way of the mutual interaction of the latch portion 35 with one of the recesses 35a, 35b, the slider 32 can be interlocked either in the extended position 32a or in the retracted position 32b. In addition, the spring 34 also comprises two wings 36 extending at an angle from the plane surface of the spring 34 and extending into the receptacle 20 when the fastener 14 is in its closed configuration 14d. The wings 36 provide a particular pressure onto the injector 60 to keep the injector 60 well seated and fixed in the receptacle 20. The slider 32 forms a kind of a U-shaped receptacle for the injector 60, in particular for the cartridge's base 74. By closing the fastener 14, hence by transferring and pivoting the fastener 14 in the closed configuration 14d, in which the slider 32 is in its extended position 32a, the fastener 14 is also in a release configuration 14a as shown in FIG. 22.

The present embodiment as shown in FIGS. 1-25 particularly demonstrates the concept of the present invention with the injector 60 fastened in the receptacle 20 while it is exclusively the cartridge 70 which is displaceable between the undeployed and deployed configuration 4, 6 through its interaction with the fastener's 14 slider 32. It is generally conceivable, that it is in fact the cartridge 70 which is fixedly attachable to the housing 12 while it is the injector 60 that is displaceable between the undeployed configuration 4 and the deployed configuration 6 relative to the cartridge 70. In other embodiments it is even conceivable that both, cartridge 70 and injector 60 are displaceable relative to the housing 12 and relative to each other during a transfer from the undeployed configuration 4 to the deployed configuration 6; and vice versa.

LIST OF REFERENCE NUMBERS 1 deploy direction
2 insert direction
4 undeployed configuration
6 deployed configuration
8 locking direction
10 drug delivery device
12 housing
14 fastener
14a release configuration
14b locking configuration
14c opened configuration
14d closed configuration
15 lid
16 hinge
18 pivot axis
20 receptacle
21 sidewall
22 recessed structure
24 guide section
30 base portion
32 slider
32a extended position
32b retracted position
33 ripples
34 spring
35 latch portion
36 wing
38 guiding pin
40 stopper
40a release configuration
40b stop configuration
41 axis
42 leg
43 stop portion
44 beveled end
45 stop face
48 stop face
50 sliding groove
52 locking portion
54 beveled portion
60 injector
61 base
62 mating structure
63 track
64 flexible tube
65 injection needle
66 piston
67 conduct
67a protector
68 injector fluid coupling
68a cannula
70 cartridge
71 housing
72 linear guiding
74 base
75 front face
76 socket
77 O-ring
78 groove
79 groove
80 reservoir
81 flexible bag
82 sealing disc
84 insert
85 through opening
86 fluid channel
90 cartridge fluid coupling
100 feeder member
104 injection drive
106 delivery drive

The invention claimed is:

1. A drug delivery device for dispensing a liquid medicament, the drug delivery device comprising:
a housing having at least one feeder member;
a disposable injector comprising a base, an injection needle, a flexible tube and an injector fluid coupling, wherein the injection needle is in fluid communication with the fluid coupling via the flexible tube and wherein the injection needle is configured to pierce a skin of a patient and is arranged on or in the base and is displaceable relative to the base; and
a disposable cartridge comprising a reservoir at least partially filled with the liquid medicament and comprising a cartridge fluid coupling in fluid communication with the reservoir,
wherein the injector and the cartridge are separate,
wherein the injector is releasably attachable to the housing,
wherein the cartridge is releasably attachable to the housing,
wherein, in an undeployed configuration, in which the injector and the cartridge are attached to the housing, the injector fluid coupling and the cartridge fluid coupling are disconnected,
wherein the base comprises a mating structure configured to engage with the housing for fastening the base to the housing; and
wherein one of the injector or the cartridge is displaceable relative to the other one of the injector or the cartridge from the undeployed configuration into a deployed configuration while attached to the housing, wherein when in the deployed configuration the injector fluid coupling and the cartridge fluid coupling are in fluid communication.

2. The drug delivery device according to claim 1, further comprising a configurable fastener to releasably fasten at least one of the injector or the cartridge to the housing.

3. The drug delivery device according to claim 2, wherein one of the injector or the cartridge is displaceable between an undeployed position and a deployed position by the fastener, which is configurable between a release configuration and a locking configuration.

4. The drug delivery device according to claim 3, wherein the fastener is pivotably connected to the housing between an opened configuration and a closed configuration, wherein one of the injector or the cartridge is attachable to the housing only when the fastener is in the opened configuration.

5. The drug delivery device according to claim 4, wherein when one of the injector or the cartridge is fastened to the housing by the fastener being in the closed configuration, the fastener is also in engagement with the other one of the injector or the cartridge.

6. The drug delivery device according to claim 5, wherein the other one of the injector or the cartridge is displaceable from the undeployed position to the deployed position by transferring the fastener from the release configuration to the locking configuration.

7. The drug delivery device according to claim 5, wherein the other one of the injector or the cartridge is displaceable from the deployed position to the undeployed position by transferring the fastener from the locking configuration to the release configuration.

8. The drug delivery device according to claim 3, wherein the fastener comprises a slider and wherein the fastener is transferable from the release configuration into the locking configuration by slidably displacing the slider from an extended position into a retracted position.

9. The drug delivery device according to claim 8, wherein the fastener comprises a pivotable lid with a free end formed by the slider, wherein in a closed configuration of the fastener, the slider at least partially enclosing one of the injector or the cartridge is retractable from the extended position into the retracted position thereby displacing the other one of the injector or the cartridge into the deployed position.

10. The drug delivery device according to claim 8, wherein one of the injector and the cartridge comprises a sliding groove to engage with a correspondingly shaped sliding pin of the slider.

11. The drug delivery device according to claim 10, wherein the sliding pin is engageable with a stopper by transferring the fastener into the a closed configuration in which the sliding pin is configured to pivot the stopper into the release configuration by displacing the slider towards the retracted position.

12. The drug delivery device according to claim 10, wherein the fastener is lockable to the housing by the sliding pin of the slider engaging with a locking portion of the sliding groove, the locking portion extending substantially perpendicular to a deploy direction.

13. The drug delivery device according to claim 2, wherein the housing comprises a receptacle to receive the other one of the injector or the cartridge, wherein the fastener is configured to releasably fix the other one of the injector or the cartridge in the receptacle.

14. The drug delivery device according to claim 3, further comprising a stopper pivotable at the housing between a release configuration and a stop configuration, and wherein the stopper is adapted to inhibit displacement of one of the injector or the cartridge beyond the undeployed position towards the deployed position.

15. The drug delivery device according to claim 1, wherein one of the injector or the cartridge comprises a linear guiding extending along a deploy direction to engage with a guide section of the housing.

16. The drug delivery device according to claim 1, wherein the liquid medicament comprises a pharmaceutically active compound.

17. A drug delivery device for dispensing a liquid medicament, the drug delivery device comprising:
    a housing having at least one feeder member;
    a disposable injector comprising a base, an injection needle, a flexible tube and an injector fluid coupling, wherein the injection needle is in fluid communication with the fluid coupling via the flexible tube, wherein the disposable injector comprises a fluid flow path for the liquid medicament, wherein the injector fluid coupling is arranged on or in the base and wherein the injection needle is arranged on or in the base and is displaceable relative to the base; and
    a disposable cartridge comprising a reservoir at least partially filled with the liquid medicament and comprising a cartridge fluid coupling in fluid communication with the reservoir,
    wherein the injector and the cartridge are separate,
    wherein the injector is releasably attachable to the housing,
    wherein the cartridge is releasably attachable to the housing,
    wherein, in an undeployed configuration, in which the injector and the cartridge are attached to the housing, the injector fluid coupling and the cartridge fluid coupling are disconnected, and
    wherein one of the injector or the cartridge is displaceable relative to the other one of the injector or the cartridge from the undeployed configuration into a deployed configuration while attached to the housing, wherein when in the deployed configuration the injector fluid coupling and the cartridge fluid coupling are in fluid communication.

18. A drug delivery device for dispensing a liquid medicament, the drug delivery device comprising:
    a housing having at least one feeder member;
    a disposable injector comprising a base, an injection needle, a flexible tube and an injector fluid coupling, wherein the injection needle is in fluid communication with the fluid coupling via the flexible tube and wherein the injection needle is configured to pierce a skin of a patient and is arranged on or in the base and is displaceable relative to the base; and
    a disposable cartridge comprising a reservoir at least partially filled with the liquid medicament and comprising a cartridge fluid coupling in fluid communication with the reservoir,
    a stopper pivotable at the housing between a release configuration and a stop configuration,
    wherein the injector and the cartridge are separate
    wherein the injector is releasably attachable to the housing,
    wherein the cartridge is releasably attachable to the housing,
    wherein, in an undeployed configuration, the injector fluid coupling and the cartridge fluid coupling are disconnected, wherein the base comprises a mating structure configured to engage with the housing for fastening the base to the housing;

wherein one of the injector or the cartridge is displaceable relative to the other one of the injector or the cartridge from the undeployed configuration into a deployed configuration while attached to the housing, wherein when in the deployed configuration the injector fluid coupling and the cartridge fluid coupling are in fluid communication; and wherein the stopper is adapted to inhibit displacement of one of the injector or the cartridge beyond the undeployed configuration towards the deployed configuration.

19. The drug delivery device according to claim 18, wherein the stopper is pivotally arranged at the housing between a release configuration and a stop configuration and wherein when in the release configuration the stopper allows displacement of one of the injector or cartridge beyond the undeployed position towards the deployed position and wherein when in the stop configuration the stopper inhibits displacement of one of the injector or cartridge beyond the undeployed position towards the deployed position.

20. The drug delivery device according to claim 19, further comprising a configurable fastener to releasably fasten at least one of the injector or cartridge to the housing and wherein the fastener is operable to pivot the stopper into the release configuration.

21. The drug delivery device according to claim 18, further comprising a configurable fastener to releasably fasten at least one of the injector or the cartridge to the housing.

* * * * *

UNITED STATES PATENT AND TRADEMARK OFFICE
CERTIFICATE OF CORRECTION

PATENT NO. : 10,569,012 B2
APPLICATION NO. : 15/104913
DATED : February 25, 2020
INVENTOR(S) : Michael Schabbach et al.

It is certified that error appears in the above-identified patent and that said Letters Patent is hereby corrected as shown below:

In the Claims

Column 19, Line 50, Claim 11, delete "the a" and insert -- a --

Column 20, Line 60, Claim 18, delete "separate" and insert -- separate, --

Signed and Sealed this
Fifth Day of May, 2020

Andrei Iancu
*Director of the United States Patent and Trademark Office*